(12) United States Patent
She (10) Patent No.: US 11,707,306 B2
(45) Date of Patent: Jul. 25, 2023

(54) FIXING BONE PLATE

(71) Applicant: Cheng Xin She, Kaohsiung (TW)

(72) Inventor: Cheng Xin She, Kaohsiung (TW)

( * ) Notice: Subject to any disclaimer, the term of this patent is extended or adjusted under 35 U.S.C. 154(b) by 0 days.

(21) Appl. No.: 15/580,714

(22) PCT Filed: Jun. 9, 2015

(86) PCT No.: PCT/CN2015/081085
§ 371 (c)(1),
(2) Date: Dec. 8, 2017

(87) PCT Pub. No.: WO2016/197328
PCT Pub. Date: Dec. 15, 2016

(65) Prior Publication Data
US 2018/0185075 A1    Jul. 5, 2018

(51) Int. Cl.
*A61B 17/80*    (2006.01)
*B33Y 10/00*    (2015.01)
*B33Y 80/00*    (2015.01)
*A61B 17/00*    (2006.01)
*A61C 7/00*    (2006.01)
*B22F 10/20*    (2021.01)
*A61B 17/56*    (2006.01)
*A61B 17/86*    (2006.01)
(Continued)

(52) U.S. Cl.
CPC .......... *A61B 17/8071* (2013.01); *A61B 17/00* (2013.01); *A61B 17/80* (2013.01); *A61B 17/8028* (2013.01); *A61B 17/8052* (2013.01); *A61B 17/86* (2013.01); *A61B 2017/00004* (2013.01); *A61B 2017/00526* (2013.01); *A61B 2017/568* (2013.01); *A61C 7/00* (2013.01); *A61L 31/022* (2013.01); *A61L 31/148* (2013.01); *A61L 2430/02* (2013.01); *B22F 10/20* (2021.01); *B33Y 10/00* (2014.12); *B33Y 80/00* (2014.12)

(58) Field of Classification Search
CPC ................ A61B 17/58; A61B 17/8028; A61B 2017/00004; A61B 17/80; A61B 2017/568; A61B 17/8061; A61B 2034/108; A61F 2210/0004
See application file for complete search history.

(56) References Cited

U.S. PATENT DOCUMENTS

| | | | | |
|---|---|---|---|---|
| 4,338,926 A | * | 7/1982 | Kummer ................ | A61B 17/80 606/62 |
| 4,403,607 A | * | 9/1983 | Woo ........................ | A61B 17/80 606/70 |

(Continued)

*Primary Examiner* — David W Bates
(74) *Attorney, Agent, or Firm* — Che-Yang Chen; Law Office of Michael Chen (57) ABSTRACT

Disclosed is a fixing bone plate, which comprises a plate body. The plate body is provided with a plate main part and a locking portion passing through the plate body. The plate main part is connected to the locking portion at the corresponding two ends of the plate body. The fixing bone plate also comprises an attachment portion. The attachment portion is provided with a bone attachment surface. The attachment portion is disposed on the other side of the locking portion. The plate body can be manufactured by using a metal laser additive manufacturing technique or a 3D metal printing technique. The fixing bone plate can be accurately positioned and stably combined with a human bone according to morphological characteristics of bones.

16 Claims, 6 Drawing Sheets

(51) Int. Cl.
*A61L 31/02* (2006.01)
*A61L 31/14* (2006.01)

(56) References Cited

U.S. PATENT DOCUMENTS

| | | | | |
|---|---|---|---|---|
| 5,013,315 A * | 5/1991 | Barrows | ............... | A61B 17/80 |
| | | | | 606/71 |
| 5,108,399 A * | 4/1992 | Eitenmuller | ....... | A61B 17/8047 |
| | | | | 606/298 |
| 5,474,553 A * | 12/1995 | Baumgart | ............... | A61B 17/80 |
| | | | | 606/309 |
| 5,702,396 A * | 12/1997 | Hoenig | ................. | A61B 17/80 |
| | | | | 606/280 |
| 6,344,042 B1 * | 2/2002 | Curtis | ............... | A61B 17/0401 |
| | | | | 606/232 |
| 6,533,454 B1 * | 3/2003 | Kaikkonen | ........... | A61B 17/68 |
| | | | | 378/205 |
| 6,738,657 B1 * | 5/2004 | Franklin | ................ | B33Y 50/02 |
| | | | | 600/429 |
| 8,241,297 B2 * | 8/2012 | Ashman | ............ | A61B 17/1796 |
| | | | | 206/206 |
| 9,675,400 B2 * | 6/2017 | Katrana | ................ | A61B 17/282 |
| 2002/0004660 A1 * | 1/2002 | Henniges | ........... | A61B 17/1655 |
| | | | | 606/86 B |
| 2002/0128654 A1 * | 9/2002 | Steger | ................ | A61B 17/8047 |
| | | | | 606/291 |
| 2003/0004515 A1 * | 1/2003 | Curtis | ................... | A61B 17/80 |
| | | | | 606/291 |
| 2005/0177162 A1 * | 8/2005 | McLeod | ............. | A61B 17/842 |
| | | | | 606/70 |
| 2007/0162019 A1 * | 7/2007 | Burns | ................ | A61B 17/8047 |
| | | | | 606/281 |
| 2008/0114370 A1 * | 5/2008 | Schoenefeld | ...... | A61B 17/1721 |
| | | | | 606/96 |
| 2010/0004691 A1 * | 1/2010 | Amato | ................... | A61B 17/80 |
| | | | | 606/280 |
| 2010/0130959 A1 * | 5/2010 | Boyd | .................... | A61B 17/60 |
| | | | | 604/513 |
| 2011/0178465 A1 * | 7/2011 | Boyd | .................... | A61B 17/60 |
| | | | | 604/175 |
| 2011/0269100 A1 * | 11/2011 | Furrer | .................... | A61C 8/0031 |
| | | | | 433/72 |
| 2012/0285002 A1 * | 11/2012 | Lin | ....................... | A61B 34/10 |
| | | | | 29/592 |
| 2015/0051650 A1 * | 2/2015 | Verstreken | .......... | A61B 17/151 |
| | | | | 606/281 |
| 2015/0051876 A1 * | 2/2015 | Rueber | ................. | A61B 17/80 |
| | | | | 703/1 |
| 2015/0216571 A1 * | 8/2015 | Impellizzeri | ...... | A61B 17/8028 |
| | | | | 606/289 |
| 2015/0327899 A1 * | 11/2015 | Early | ................ | A61B 17/8085 |
| | | | | 606/280 |
| 2016/0192970 A1 * | 7/2016 | Dayton | .............. | A61B 17/8085 |
| | | | | 606/281 |
| 2016/0287335 A1 * | 10/2016 | Goto | ...................... | A61B 17/17 |
| 2017/0143392 A1 * | 5/2017 | Weinzweig | ........... | A61B 17/80 |
| 2017/0231673 A1 * | 8/2017 | Hirata | ............... | A61B 17/8061 |
| | | | | 606/291 |
| 2018/0036050 A1 * | 2/2018 | Mishra | ..................... | A61F 2/28 |
| 2018/0168811 A1 * | 6/2018 | Ranganathan | ........... | A61F 2/28 |

\* cited by examiner

FIXING BONE PLATE

CROSS REFERENCE OF RELATED APPLICATION

This is a U.S. National Stage under 35 U.S.C. 371 of the International Application Number PCT/CN2015/081085, filed Jun. 9, 2015. The afore-mentioned patent application is hereby incorporated by reference in its entirety.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a fixing bone plate, particularly to a fixing bone plate device used in dental surgery, orthognathic surgery and facial bone contouring surgery.

Description of Related Arts

Orthognathic surgery is well-known for amending orthognathic and facial configuration and fixing problems in growth and development, improving sleep apnea, easing temporomandibular joint and muscle disorders (TMJ disorders), adjusting malocclusion led by bone problems, or performing surgeries when an orthodontic treatment is not able to rectify easily by dental braces; in addition, orthognathic surgery is also performed to treat congenital conditions such as cleft lip and cleft palate. Orthognathic surgery is performed by an oral and maxillofacial surgeon in collaboration with an orthodontist. When an orthognathic surgery is performed, the original palatine bone is cut open, adjusted, and then re-joined by using bone plates and bone nails for shaping, during which medical materials such as metal bone plates, screws, bone nails, or stainless wires are often required, so that the orthognathic and facial areas can be fixed and shaped. However, there is no standard metal bone plate existing currently that features a complete attachment to bones, hence, the surgeon and the orthodontist will need to lock the bone plate based on experiences by hand to adjust the angle for locking the bone plate, which results in a prolonged operation and increases the degree of difficulty for surgery. It is not rare to find that a patient suffers from malocclusions after the surgery, for example, fail to reach to a predetermined biting location, overbite, or poor bite, which may be led by a prolonged surgery or improper experiences, particularly in using a fixing bone plate to rectify palatine bone.

A publicized patent application, TW201313207 titled as "Hinged fixation devices for combined upper jaw correction", claims the fixation device comprising: a first footplate including a first footplate body configured to be attached to a first bone portion; a second footplate including a second footplate body configured to be attached to a second bone portion; and a joining element coupled between the first and second footplate bodies, the joining element including a hinge that defines a pivot axis about which the first footplate body is passively rotatable with respect to the second footplate body in response to a force applied to the second footplate body. As disclosed in TW201313207, the joined angle between the plate and the bone is adjusted by rotating the hinge, which cannot precisely make sure of the location for cutting and the drilling position for the fixing bone plate as well. Therefore, TW201313207 is not able to align precisely the bone plate with the bone for a secured fixation as it cannot align precisely based on morphological characteristics of bones.

A publicized patent application, TW201404364 titled as "Orthodontic treatment anchoring module and correcting board and surgical navigating device thereof", claims the module comprising two bone screws and a correcting board. Each bone screw has an exposed section and an implanted section which communicate with each other. The exposed section of the bone screw has a first pivot-locking portion, a closing portion and a second pivot-locking portion, with the first pivot-locking portion is adjacent to the implanted section of the bone screw, with the closing portion is set between the first pivot-locking portion and the second pivot-locking portion. The peripheral surface of the first pivot-locking portion is non-circle. The correcting board has a bridge-connecting section, a positioning section and a slew-closing section, with the bridge-connecting section is set between the positioning section and the slew-closing section, with the bridge-connecting section has at least one hooking portion, with the positioning section and the slew-closing section receives with the closing portion of the two bone screws. The two bone screws are guided and screwed into appropriate position of the jawbone by operating with a surgical navigating device, to make the correcting board couple with the two bone screws. As disclosed in TW201404364, the correcting board and the bone screws are not able to adjust the angle of bone plate to have the bone plate precisely attached to the bone, therefore, it is possibly that the patient may suffer from incorrect biting, overbite, poor bite and etc. after the surgery.

A published patent TW I398241, titled as "Dental maxillary microimplant, is made of a plate and a correction accessory. The plate is installed into a keratinized epithelium of a maxilla in a correction patient's mouth, and then first and second locking elements are passed through first and second locking holes formed at both ends of the plate respectively to secure the plate to the maxilla, and finally a third locking element is passed through a fourth locking hole formed on the correction accessory and a third locking hole formed on the plate to secure the correction accessory to the maxilla. The plate disclosed in TWI398241 cannot solve the existing problem, that is, to align precisely the bone plate with the bone for a secured fixation as it cannot align precisely based on morphological characteristics of bones.

Therefore, the invention aims at providing a fixing bone plate capable of being used in dental surgery, orthognathic surgery and facial bone contouring surgery, moreover, the fixing bone plate provided in the present invention is able to align precisely based on features of bones and attach securely thereon, thereby solving aforementioned problems in orthognathic surgery, that is, the oral and maxillofacial surgeon and the orthodontist need to manually adjust and lock the fixing bone plate.

SUMMARY OF THE PRESENT INVENTION

One purpose of the invention is to provide a fixing bone plate, which can be used in dental surgery, orthognathic surgery and facial bone contouring surgery, and can attach to human bones based on bone features so as to achieve an effect of precisely positioning and securely attachment.

Another purpose of the invention is to provide a fixing bone plate, which includes an attachment portion having a bone attachment surface, and the bone attachment surface can be calculated by a computer process, so that the fixing bone plate can be designed to precisely align with and securely attach to human bones.

To achieve aforementioned purposes, the invention provides a fixing bone plate, which includes a plate body having a plate main part and a locking portion passing through the plate body, wherein the plate main part is connected to the locking portion at the corresponding two ends of the plate body. The plate body further includes an attachment portion disposed on the other side of the locking portion.

In one embodiment disclosed in the invention, the plate main part may be a plane plate or a cured plate.

In one embodiment disclosed in the invention, the locking portion may be an opening or a screw hole.

In one embodiment disclosed in the invention, the attachment portion may be a guide pin or a pad.

In one embodiment disclosed in the invention, the bone attachment surface may be a plane surface or a curved surface.

In one embodiment disclosed in the invention, the plate body may be made of medical titanium alloys or bioabsorbable materials.

In one embodiment disclosed in the invention, the attachment portion may be made of medical titanium alloys or bioabsorbable materials.

In one embodiment disclosed in the invention, the fixing bone plate further includes an engagement device for securing the fixing bone plate onto bones.

In one embodiment disclosed in the invention, the engagement device may be a bone nail, a rivet or a screw.

In one embodiment disclosed in the invention, the plate body and the attachment portion are made by using laser additive manufacturing technique or 3D metal printing technique.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustration only, and not as a definition of the invention.

DETAILED DESCRIPTION OF THE PREFERRED EMBODIMENT

Although some words has been used in the specification and subsequent claims to refer to particular components, person having ordinary skill in the art will appreciates that manufacturers may use different terms to refer to a component. The specification and claims are not to be differences in the names as a way to distinguish between the components, but with differences in the function of the component as a criterion to distinguish. As mentioned throughout the specification and claims, in which the "include, has, comprise, and with" are an open-ended term, they should be interpreted as "including but not limited to".

Figure 1:
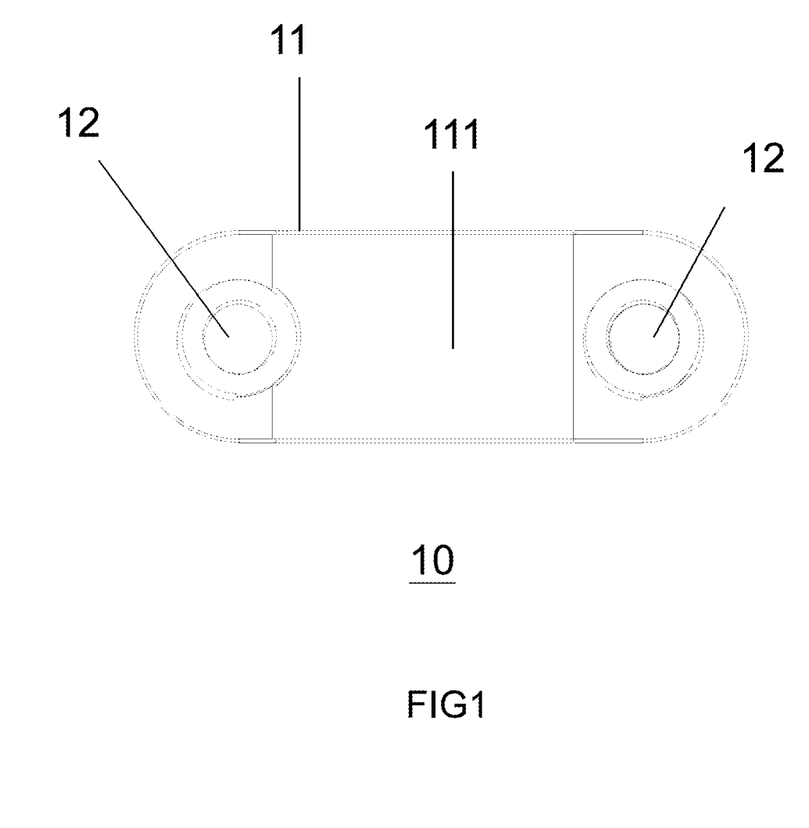
FIG. 1 is a plan schematic diagram of the fixing bone plate
Figure 2:
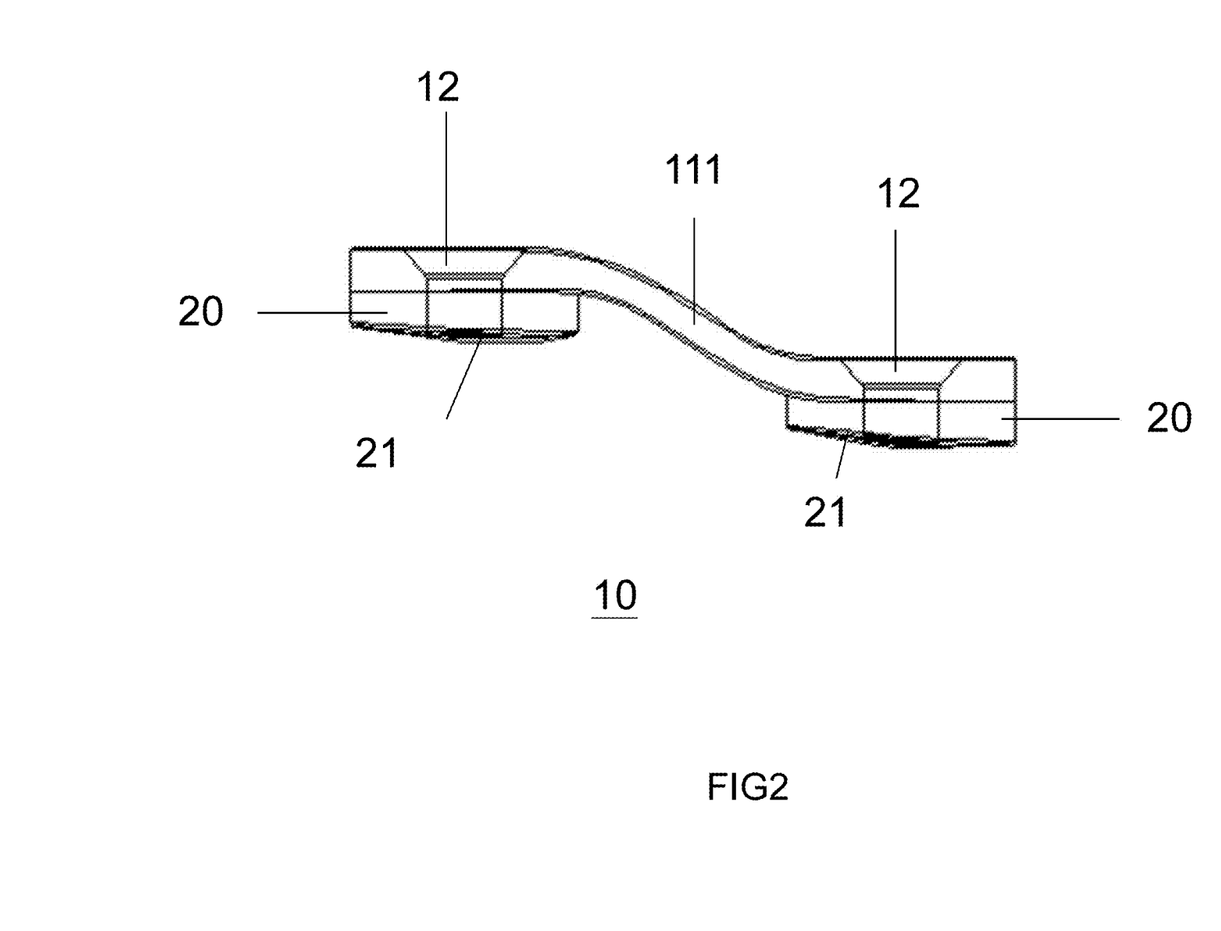
FIG. 2 is a side viewed schematic diagram of the fixing bone plate

One preferred embodiment discloses a fixing bone plate 10 as shown in FIG. 1 which is a plan schematic diagram, and in FIG. 2 which is a side viewed schematic diagram. The fixing bone plate 10 includes a plate body 11 with a plate main part 111 and a locking portion 12 passing through the plate body 11. The plate main part 111 is connected to the locking portion 12 at the corresponding two ends of the plate body 11. The fixing bone plate 10 also comprises an attachment portion 20. The attachment portion 20 is provided with a bone attachment surface 21. The attachment portion 20 is disposed on the other side of the locking portion 12.

Figure 3:
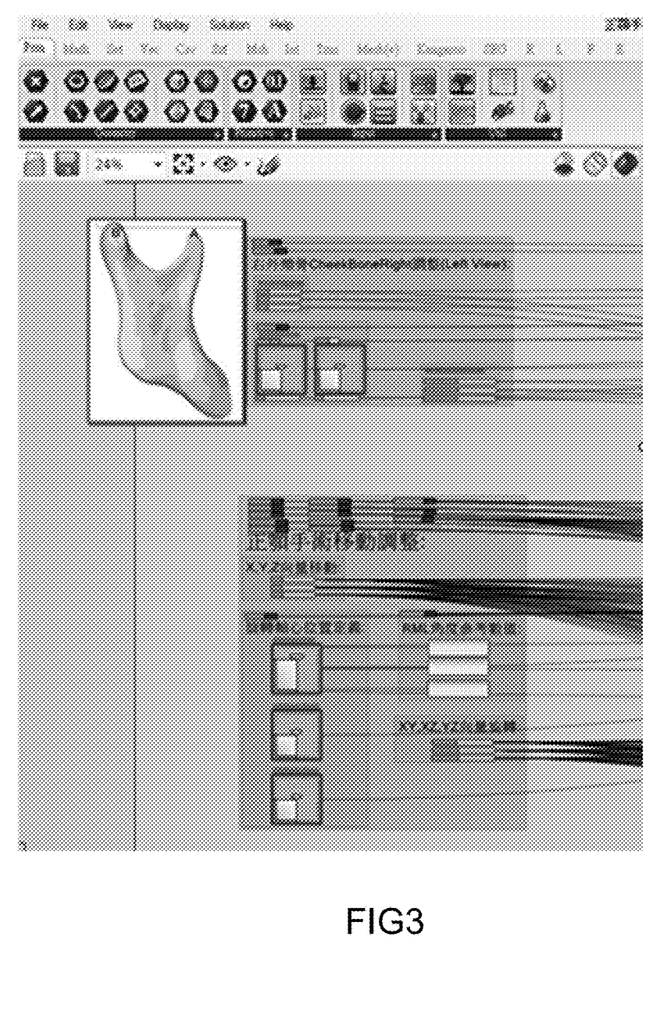
FIG. 3 is a parameter inputting diagram on simulation computer graphic software for the fixing bone plate

As shown in FIG. 2 in the preferred embodiment, the plate main part 111 is a curved plate main part, which the degree of curvature and gradient of the curve can be calculated by using a computing software of a custom graphic user interface (GUI), such as GRASSHOPPER. The commercial product like GRASSHOPPER is used to calculate axial positions of X, Y, Z and angles. As shown in FIG. 3, the stimulation computer software GRASSHOPPER calculates parameters for manufacturing the plate main part 111, and the metal laser additive manufacturing technique produces the plate main part 111, thereby forming an outlook of a bridged-shaped supportive frame for the plate main part 111. The locking portion 12 that is corresponding to the two ends of the plate body 11 can be a screw hole, which is used to lock the fixing bone plate 10. The attachment portion 20 can be a guide pin, and the bone attachment surface 21 can be a curved surface. By using a computing software of a custom graphic user interface (GUI), (such as GRASSHOPPER), the height of the attachment portion 20 and the area of the bone attachment surface 21 can be calculated, and then using the metal laser additive technique to form the attachment portion 20 and the bone attachment surface 21.

Figure 4:
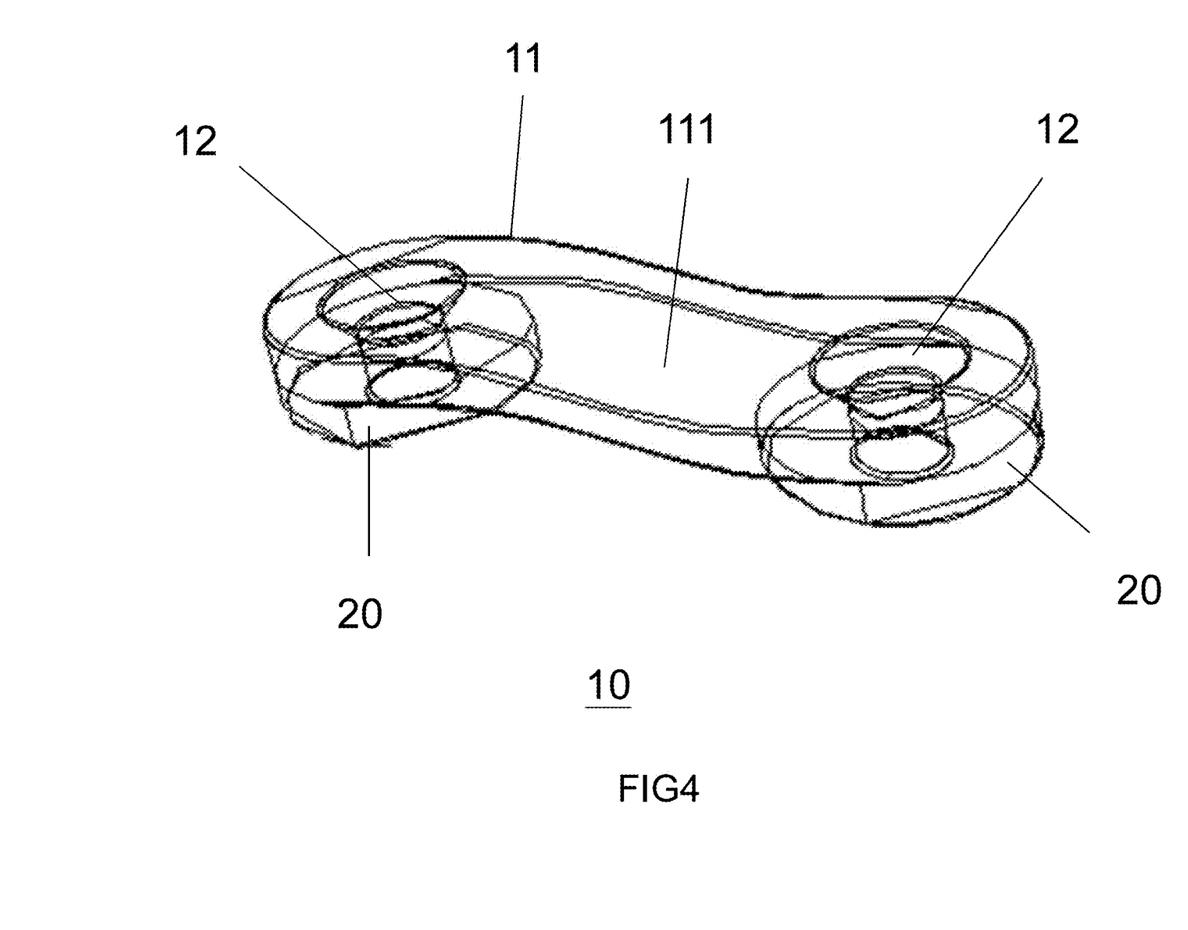
FIG. 4 is a 3D schematic diagram of the fixing bone plate

As shown in FIG. 4 which is a 3D schematic diagram of the fixing bone plate 10 of the present invention, the fixing bone plate 10 includes a plate body 11 with a plate main part 111 and a locking portion 12 passing through the plate body 11. The plate main part 111 is connected to the locking portion 12 at the corresponding two ends of the plate body 11. The fixing bone plate 10 also comprises an attachment portion 20. Wherein the plate body 11 is made of medical titanium alloys (Ti-6Al-4V), and the attachment portion 20 is made of medical titanium alloys (Ti-6Al-4V) as well.

As disclosed in the aforementioned embodiment, the plate main part 111 may be replaced by a plane plate main part; the locking portion 12 may be replaced by an opening; the attachment portion 20 may be replaced by a pad; the bone attachment surface 21 may be replaced by a plane surface; the plate body 11 may be replaced by one kind of bioabsorbable materials; the attachment portion 20 may be replaced by one kind of bioabsorbable materials; and the plate body 11 and the attachment portion 20 may be manufactured using 3D metal printing technique.

Figure 5:
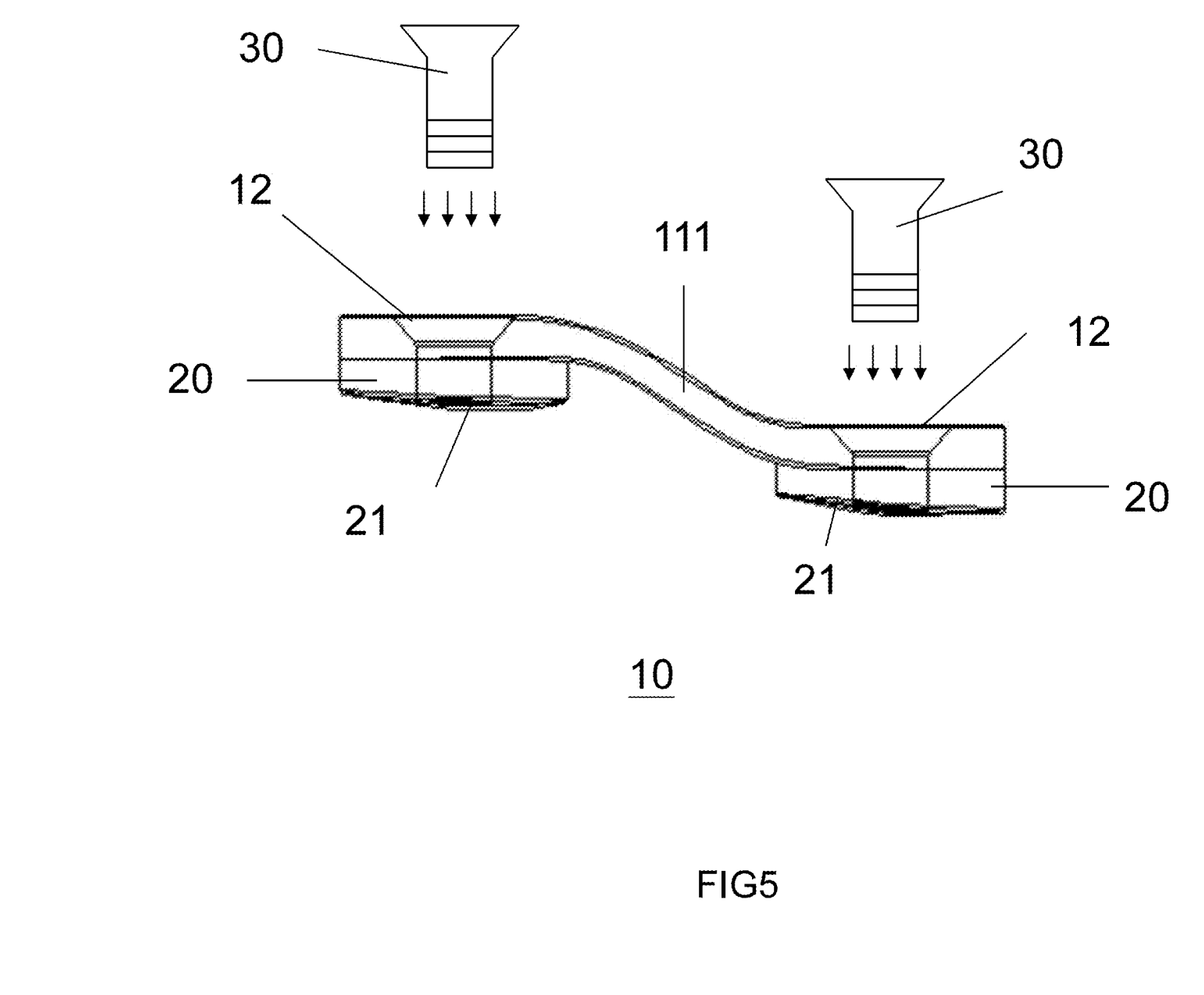
FIG. 5 is a combined schematic diagram combining the fixing bone plate with the engagement device

As shown in FIG. 5 which is another preferred embodiment, the fixing bone plate 10 in the present invention and an engagement device 30 are combined as illustrated in FIG. 5. The fixing bone plate 10 includes a plate body 11 with a plate main part 111 and a locking portion 12 passing through the plate body 11. The locking portion 12 is arranged at two ends of the plate body 11, and the plate main part 111 is used for connecting the locking portion 12 at the corresponding two ends of the plate body 11. The fixing bone plate 10 also comprises an attachment portion 20, which is provided with a bone attachment surface 21. The attachment portion 21 is disposed on the other side of the locking portion 12. Notably, the fixing bone plate 10 further includes an engagement device 30 by which the fixing bone plate 10 is connected securely to human bones.

As shown in FIG. 5, the plate main part 111 may be a curved plate main part, which the X, Y, and Z axial positions and angles can be calculated by a computer graphic interface software, and then manufactured by metal laser additive technique, thereby forming a bridged-shaped supportive appearance of the plate main part 111. The locking portion 12 that corresponds to the two ends of the plate body 11 may be a screw hole, which is able to lock the fixing bone plate 10. The attachment portion 20 may be a guide pin and has a bone attachment surface 21, which may be a curved surface. By using computer software (such as GRASSHOPPER), the height of the attachment portion 20 and the area of the bone attachment surface 21 can be calculated, and then produced by using metal laser additive technique to form the attachment portion 20 and the bone attachment surface 21 accordingly. The fixing bone plate 10 further includes an engagement device 30, by which the fixing bone plate 10 is fixed to human bones. Notably, the engagement device 30 may be a bone nail, the plate body 11 may be made of medial titanium alloys (Ti-6Al-4V), and the attachment portion 20 may also be made of medial titanium alloys (Ti-6Al-4V).

As disclosed in the aforementioned embodiment, the plate main part 111 may be replaced by a plane plate main part; the locking portion 12 may be replaced by an opening; the attachment portion 20 may be replaced by a pad; the bone attachment surface 21 may be replaced by a plane surface; the plate body 11 may be replaced by one kind of bioabsorbable materials; the attachment portion 20 may be replaced by one kind of bioabsorbable materials; the engagement device 30 may be replaced by a rivet or a screw; and the plate body 11 and the attachment portion 20 may be manufactured using 3D metal printing technique.

Figure 6:
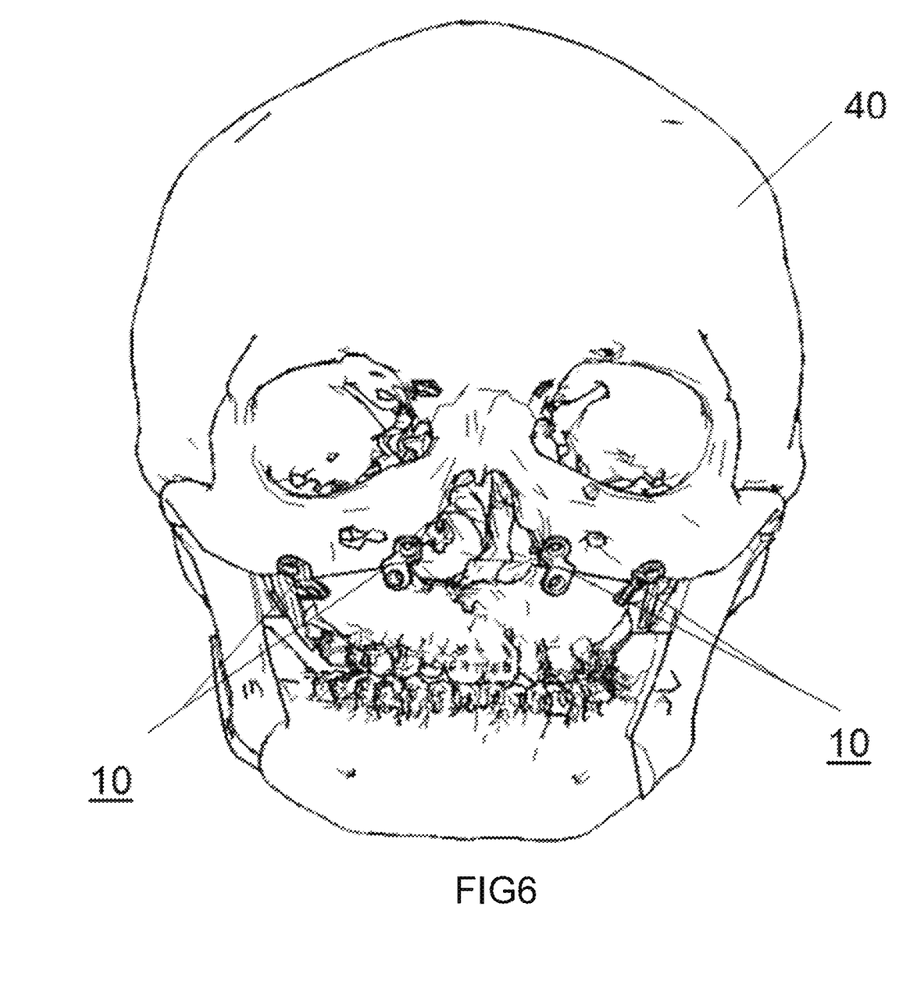
FIG. 6 is a combined schematic diagram of the fixing bone plate attached onto human bones.

As shown in FIG. 6 which is another preferred embodiment, the fixing bone plate 10 is attached onto a human bone. When an orthognathic surgery is performed, bone needs to be cut and adjusted and then re-joined by using a bone plate and bone nails to model the face. As illustrated in FIG. 6, the fixing bone plate 10 is fixed onto the skull 40 based on the features of upper/lower jaw and cheek bones by using bone nails, thereby precisely aligning the fixing bone plate 10 according to the morphological characteristics of the bone on the skull 40 in a secured manner.

There have thus been shown and described a fixing bone plate. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention.

What is claimed is:

1. A fixing bone plate for fixing onto one or more bones with at least one engagement device for re-joining the one or more bones, comprising:
   a plate body having semicircular first and second end portions and two locking portions, each having a first side and a second side, passing through the first end portion and the second end portion of the plate body respectively and each extending from the first side to the second side for fixing the fixing bone plate onto the one or more bones by the at least one engagement device and a plate main part extended between the two locking portions, wherein the plate main part is a curved part having a predetermined thickness and a predetermined curvature, wherein a degree of the predetermined curvature and gradient of the curvature of the plate main part is determined by a computer graphic interface software which calculates axial positions of X, Y and Z axial positions and an inclination angle of the plate main part according to the one or more bones that the fixing bone plate to be fixed; and
   two attachment portions, each having a diameter equal to a diameter of the semicircular first and second end portions of the plate body, integrally provided on the first and second end portions of the plate body respectively and protruding from the second side of the plate body such that the two locking portions pass through the two attachment portions respectively, wherein each of the attachment portions is a guide element selected from the group consisting of guide pin and guide pad and has a thicker edge and a thinner edge, wherein each of the attachment portions has a bone attachment surface which is a curved surface for positioning at a position of one of the one or more bones, wherein the two bone attachment surfaces are configured to be noncoplanar with each other and are parallel with each other, wherein the curved surface of each of the bone attachment surfaces is gradually inclined from the thicker edge to the thinner edge of the respective attachment portion along a longitudinal direction of the plate body to define a gradient of the curved surface which is provided corresponding to the degree of the predetermined curvature and gradient of the curvature and the inclination angle of the plate main part of the plate body, wherein the gradient of the curved surface, a height and an area of the bone attachment surface of each of the attachment portions are determined by the computer graphic interface software which calculates the axial positions of X, Y and Z axial positions according to the one or more bones that the fixing bone plate to be fixed and the attachment surfaces to be attached so as to obtain parameters for making the plate main part to form a bridged-shaped supportive frame.

2. The fixing bone plate, as recited in claim 1, wherein the computer graphic interface software is GRASSHOPPER.

3. The fixing bone plate, as recited in claim 1, wherein the two attachment portions are formed on the two end portions of the plate body by a metal laser additive method.

4. The fixing bone plate, as recited in claim 1, wherein the plate body and the two attachment portions are made of medical titanium alloys.

5. The fixing bone plate, as recited in claim 3, wherein the plate body and the two attachment portions are made of medical titanium alloy.

6. The fixing bone plate, as recited in claim 4, wherein the medical titanium alloy is Ti-6Al-4V.

7. The fixing bone plate, as recited in claim 5, wherein the medical titanium alloy is Ti-6Al-4V.

8. The fixing bone plate, as recited in claim 1, wherein the plate body and the two attachment portions are produced by a 3D metal printing method.

9. The fixing bone plate, as recited in claim 1, wherein the plate body and the two attachment portions are made of a bioabsorbable material.

10. The fixing bone plate, as recited in claim 1, wherein the locking portions are locking holes for elements selected from the group consisting of bone nails, rivets and screws to securely connect the fixing bone plate to the one or more bones.

11. The fixing bone plate, as recited in claim 3, wherein the locking portions are locking holes for elements selected from the group consisting of bone nails, rivets and screws to securely connect the fixing bone plate to the one or more bones.

12. The fixing bone plate, as recited in claim 8, wherein the locking portions are locking holes for elements selected from the group consisting of bone nails, rivets and screws to securely connect the fixing bone plate to the one or more bones.

13. The fixing bone plate, as recited in claim 1, wherein at least one of the bone attachment surfaces is a curved convex surface.

14. The fixing bone plate, as recited in claim 3, wherein at least one of the bone attachment surfaces is a curved convex surface.

15. The fixing bone plate, as recited in claim 8 wherein at least one of the bone attachment surfaces is a curved convex surface.

16. The fixing bone plate, as recited in claim 10 wherein at least one of the bone attachment surfaces is a curved convex surface.

\* \* \* \* \*